(12) United States Patent
Cox et al.

(10) Patent No.: US 8,945,660 B2
(45) Date of Patent: Feb. 3, 2015

(54) EDIBLE FOAM PRODUCT FOR THE TREATMENT OR PREVENTION OF OBESITY

(75) Inventors: Andrew Richard Cox, Sharnbrook (GB); Petrus Wilhelmus N de Groot, Vlaardingen (NL); Sergey Michailovich Melnikov, Vlaardingen (NL); Simeon Dobrev Stoyanov, Vlaardingen (NL)

(73) Assignee: KSF Acquisition Corporation, West Palm Beach, FL (US)

( * ) Notice: Subject to any disclaimer, the term of this patent is extended or adjusted under 35 U.S.C. 154(b) by 557 days.

(21) Appl. No.: 12/445,478

(22) PCT Filed: Oct. 1, 2007

(86) PCT No.: PCT/EP2007/060354
§ 371 (c)(1),
(2), (4) Date: Apr. 14, 2009

(87) PCT Pub. No.: WO2008/046729
PCT Pub. Date: Apr. 24, 2008

(65) Prior Publication Data
US 2010/0034753 A1    Feb. 11, 2010

(30) Foreign Application Priority Data
Oct. 17, 2006   (EP) .................... 06122405

(51) Int. Cl.
| A23L 1/00 | (2006.01) |
| A23G 1/04 | (2006.01) |
| A23J 1/00 | (2006.01) |
| A23G 3/00 | (2006.01) |
| A23D 7/00 | (2006.01) |
| A23L 1/29 | (2006.01) |
| A23L 1/305 | (2006.01) |
| A61K 9/00 | (2006.01) |
| A61K 9/12 | (2006.01) |

(52) U.S. Cl.
CPC .............. *A23L 1/293* (2013.01); *A23L 1/0097* (2013.01); *A23L 1/296* (2013.01); *A23L 1/3058* (2013.01); *A61K 9/0056* (2013.01); *A23V 2002/00* (2013.01); *A61K 9/12* (2013.01)
USPC ............ 426/631; 426/656; 426/658; 426/601

(58) Field of Classification Search
CPC ........... A23V 2002/00; A23V 2250/54; A23V 2200/3324; A23G 9/46; A23G 1/30; A23L 1/0097; A23L 1/293
USPC .......................... 426/564, 631, 656, 658, 601
See application file for complete search history.

(56) References Cited

U.S. PATENT DOCUMENTS

| 2,965,493 | A |  | 12/1960 | Mancuso et al. |
| 3,809,764 | A |  | 5/1974 | Gabby et al. .................. 426/163 |
| 3,968,266 | A |  | 7/1976 | Baugher |
| 4,146,652 | A |  | 3/1979 | Kahn et al. |
| 4,154,863 | A |  | 5/1979 | Kahn et al. |
| 4,208,444 | A | * | 6/1980 | Gilmore et al. ............... 426/570 |
| 4,421,778 | A |  | 12/1983 | Kahn et al. |
| 4,612,852 | A |  | 9/1986 | Price et al. |
| 4,631,196 | A |  | 12/1986 | Zeller |
| 4,770,892 | A |  | 9/1988 | Grealy et al. |
| 4,793,279 | A |  | 12/1988 | Grenier |
| 4,828,854 | A |  | 5/1989 | Beer |
| 4,855,156 | A | * | 8/1989 | Singer et al. .................. 426/565 |
| 5,000,974 | A |  | 3/1991 | Albersmann ................. 426/564 |
| 5,004,623 | A |  | 4/1991 | Giddey et al. |
| 5,395,877 | A |  | 3/1995 | Pucknat et al. |
| 5,493,957 | A |  | 2/1996 | Kennedy et al. |

(Continued)

FOREIGN PATENT DOCUMENTS

| DE | 19617568 C1 | 12/1997 |
| EP | 0238330 A2 | 9/1987 |

(Continued)

OTHER PUBLICATIONS

PCT International Search Report in a PCT application PCT/EP2007. 060354.

(Continued)

*Primary Examiner* — Abigail Fisher
(74) *Attorney, Agent, or Firm* — Vinson & Elkins

(57) ABSTRACT

The present invention relates to an edible foam product that can advantageously be used in the treatment or prevention of obesity. More particularly, the present invention provides an edible foam product of pourable or spoonable consistency having an overrun of at least 100%, said foam product containing at least 60 wt. % of water, from 1 to 7 wt. % of protein and from 1 to 20 wt. % of carbohydrates, and further being characterized by a high in-mouth stability as evidenced by a reduction in overrun of less than 35% under in-mouth shear conditions and a high gastric stability as evidenced by a $t_{1/2} > 30$ minutes, $t_{1/2}$ representing the time needed to achieve a reduction in overrun of 50% under gastric conditions. Another aspect of the invention relates to the use of an edible foam product in the treatment or prevention of overweight or obesity, said edible foam product having a pourable or spoonable consistency, an overrun of at least 100% and a high gastric stability as evidenced by $t_{1/2} > 30$ minutes. Yet another aspect of the invention concerns a pressurized container holding an edible liquid composition and a propellant, which liquid composition can be released from the container by activating a valve to produce an edible foam product having a pourable or spoonable consistency, an overrun of at least 100% and a high gastric stability as evidenced by $t_{1/2} > 30$ minutes.

14 Claims, 4 Drawing Sheets

(56) References Cited

U.S. PATENT DOCUMENTS

| | | | |
|---|---|---|---|
| 5,605,712 A | 2/1997 | Bertrand et al. | |
| 5,658,377 A | 8/1997 | Craig | |
| 5,688,547 A | 11/1997 | Ritchey et al. | |
| 5,789,004 A | 8/1998 | Hogan et al. | |
| 5,800,604 A | 9/1998 | Berger | |
| 6,037,380 A * | 3/2000 | Venables et al. | 514/781 |
| 6,177,103 B1 | 1/2001 | Pace et al. | |
| 6,241,812 B1 | 6/2001 | Smith et al. | |
| 6,262,128 B1 | 7/2001 | Stern et al. | |
| 6,326,046 B1 | 12/2001 | Tucker et al. | |
| 6,497,913 B1 | 12/2002 | Gray et al. | |
| 6,673,384 B1 * | 1/2004 | Villagran et al. | 426/575 |
| 6,677,318 B1 | 1/2004 | Beisel | 514/54 |
| 8,309,154 B2 | 11/2012 | Cai et al. | |
| 8,597,708 B2 | 12/2013 | Blijdenstein et al. | |
| 2003/0078172 A1 | 4/2003 | Guiramand et al. | |
| 2003/0175317 A1 | 9/2003 | Barthel et al. | |
| 2004/0185162 A1 | 9/2004 | Finnigan et al. | |
| 2005/0137115 A1 | 6/2005 | Cole et al. | |
| 2005/0222082 A1 | 10/2005 | Beisel | 514/54 |
| 2005/0266992 A1 | 12/2005 | Ohno et al. | |
| 2006/0024417 A1 * | 2/2006 | Berry et al. | 426/564 |
| 2006/0063882 A1 | 3/2006 | Velev et al. | |
| 2006/0141102 A1 * | 6/2006 | Fleming et al. | 426/100 |
| 2007/0071874 A1 | 3/2007 | Cash et al. | |
| 2010/0112179 A1 * | 5/2010 | Cox et al. | 426/564 |
| 2010/0186420 A1 * | 7/2010 | Berry et al. | 62/1 |
| 2010/0189857 A1 | 7/2010 | Blijdenstein et al. | |

FOREIGN PATENT DOCUMENTS

| | | |
|---|---|---|
| EP | 0 292 034 | 11/1988 |
| EP | 0348503 B1 | 1/1990 |
| EP | 522704 A2 * | 1/1993 |
| EP | 0930017 A1 | 7/1999 |
| EP | 1079021 A1 | 2/2001 |
| EP | 1166655 A1 | 1/2002 |
| EP | 1295594 A1 | 3/2003 |
| EP | 1582105 A1 | 10/2005 |
| EP | 1623631 B1 | 4/2007 |
| EP | 1621084 B1 | 4/2008 |
| EP | 2505076 A1 | 10/2012 |
| EP | 2505077 A1 | 10/2012 |
| EP | 2505078 A1 | 10/2012 |
| EP | 2505079 A1 | 10/2012 |
| GB | 2211392 A | 7/1989 |
| GB | 2377155 A | 1/2003 |
| JP | 53104767 A | 9/1978 |
| JP | 60099333 A | 6/1985 |
| JP | 1148164 A | 6/1989 |
| JP | 568486 A | 3/1993 |
| JP | 11299435 A | 11/1999 |
| JP | 2002161161 A2 | 6/2002 |
| JP | 2002345401 A | 12/2002 |
| KR | 950006071 B1 | 6/1995 |
| WO | WO 89/05587 A3 | 6/1989 |
| WO | WO8905587 | 6/1989 |
| WO | WO0001246 | 1/2000 |
| WO | WO0106865 A1 | 2/2001 |
| WO | WO 03/040190 A1 | 5/2003 |
| WO | 2004/017746 | 3/2004 |
| WO | WO 2005/082507 A1 | 9/2005 |
| WO | WO 2006/007393 A1 | 1/2006 |
| WO | 2006/067064 | 6/2006 |
| WO | WO 2007/068344 A1 | 6/2007 |

OTHER PUBLICATIONS

Rolls et al., "Increasing the volume of a food by incorporating air affects satiety in men[1-3]", American Journal of Clinical Nutrition, 2000; vol. 72, pp. 361-368.

Wanskin et al., "Bottomless Bowls: Why Visual Cues of Portion Size May Influence Intake", Obestity Reseawrch, vol. 13, No. 1, Jan. 2005, pp. 93-100.

European Search Report in an EP application EP 06 12 2405.

Calver et al., "Simple Methods to Measure Air Exchange Rates and Detect Leaks in Display and Storage Enclosures", Published in the 14th Triennial Meeting The Hague Preprints, pp. 597-609, Publ. Dec. 31, 2005.

Alargova, et al., "Scalable Synthesis of a New Class of Polymer Microrods by a Liquid-Liquid Dispersion Technique," Adv. Mater. 16:1653-1657, 2004.

Alargova, et al., "Foam Superstabilization by Polymer Microrods," Langmuir 20:10371-1-374, 2004.

Alargova, et al., "Formation of Polymer Microrods in Shear Flow by Emulsification—Solvent Attrition Mechanism," Langmuir 22:765-774, 2006.

Antova, et al., "Studies upon the synthesis of cellulose stearate under microwave heating," Carbohydrate Polymers 57:131-134, 2004.

Aqualon, "Hydroxypropylcellulose: Physical and Chemical Properties," Hercules Incorporated, 2001.

Aqualon, "Sodium Carboxymethylcellulose: Physical and Chemical Properties," Hercules Incorporated, 1999.

Arbuckle, "Ice Cream," Second Edition, The Avi Publishing Company, Inc., Westport, CT, 1972, pp. 35, 266, 284, 285.

Binks, "Particles as surfactants—similarities and differences," Curr. Opin. Colloid Interface Sci. 7:21-41, 2002.

"Cellulose, Processing," NOSB TAP Review Compiled by OMRI, Sep. 28, 2001, pp. 1-17.

Combes, et al., "Supercritical Fluid Processes," United States Statutory Invention Registration No. H1,839, Feb. 1, 2000.

Co-pending U.S. Appl. No. 12/086,095, filed Jun. 5, 2008.
Co-pending U.S. Appl. No. 12/309,307, filed Jan. 13, 2009.
Co-pending U.S. Appl. No. 12/445,579, filed Apr. 15, 2009.
Co-pending U.S. Appl. No. 12/445,582, filed Apr. 15, 2009.
Co-pending U.S. Appl. No. 12/445,583, filed Apr. 15, 2009.

Dry-Flo, United States Trademark, Registration Date Jun. 1, 2003, Published for Opposition Mar. 9, 2004.

Igoe and Hui, "Carboxymethylcellulose (CMC)" in Dictionary of Food Ingredients, Third Edition, Chapman & Hall, 1996, p. 30.

Iijima, et al., "Microcrystalline cellulose: An overview," Handbook of Hydrocolloids, Chapter 19, 2000, pp. 332-346.

Lewis, "Carboxylmethylcellulose," in Hawley's Condensed Chemical Dictionary, 15th Ed., John Wiley, NY, 2007, p. 238.

Murray and Ettelaie, "Foam stability: Proteins and nanoparticles," Curr. Opin. Colloid Interface Sci. 9:314-320, 2004.

Noble, et al., "Fabrication of 'Hairy' Colloidosomes with Shells of Polymeric Microrods," J. Am. Chem. Soc. 126:8092-8093, 2004.

Paunov, "Novel Method for Determining the Three-Phase Contact Angle of Colloid particles Adsorbed at Air-Water and Oil-Water Interfaces," Langmuir 19:7970-7976, 2003.

Pollock, "Influence of Filler/Binder Composition on the Properties of an Inert Matrix Controlled Release System," Pres. 24th Int. Sym. Cont. Rel. Bioact. Mat. Stockholm, 1997.

Ramsden, "Separation of Solids in the Surface-layers of Solutions and 'Suspensions'—Preliminary Account," Physiologische Abtheilnug, 156-164, 1903.

Rekhi and Jambhekar, "Ethylcellulose—A Polymer Review," Drug Dev. Ind. Pharm. 21:61-77, 1995.

Rousseau and Hodge, "Stabilization of water-in-oil emulsions with continuous phase crystals," Colloids Surf., A 260:229-237, 2005.

Watson, et al., "The Effect of Solvent and Fiber Treatment on the Deposition of Organic Silane Solutions Using THF and Acetone," J. Colloid Interface Sci. 241:32-44, 2001.

Whitesides and Grzybowski, "Self-Assembly at All Scales," Science 295:2418-2421, 2002.

Wu, et al., "SU-8 Hydrophilic Modification by Forming Copolymer with Hydrophilic Epoxy Molecule," 7th Int. Conf. Min. Chem. Biochem. Anal. Sys. 2003, pp. 1117-1120.

* cited by examiner

EDIBLE FOAM PRODUCT FOR THE TREATMENT OR PREVENTION OF OBESITY

TECHNICAL FIELD OF THE INVENTION

The present invention relates to an edible foam product with high in-mouth and gastric stability and to its use in the treatment or prevention of obesity.

The invention also concerns a pressurised container holding an edible liquid composition and a propellant, which liquid composition can be released from the container by activating a valve to produce an edible foam with high in-mouth and gastric stability.

BACKGROUND OF THE INVENTION

Large consumer studies show that between 1977 and 1996 in the United States average portion sizes for key food products grew markedly (Nielsen S J, Popkin B M, JAMA 2003; 289:450-453). The actual increase of portion sizes for a number of food products is shown in the following table (from the aforementioned article by Nielsen et al.):

| Food product | Increase in volume (ml) | Increase in kcal |
|---|---|---|
| Snacks | 18 | 93 |
| Hamburgers | 38 | 97 |
| French fries | 15 | 68 |
| Soft/fruit drinks | 200 | 49 |

Together with the trend of decreasing physical activity, the increase in portion sizes is believed to have contributed significantly to the obesity boom.

Apart from increasing the total calorie intake, the increase of portion size has an additional important consequence, since altering visual cues (e.g. portion size) of how much is eaten influences the intake and satiety perception. A recent study (Wansink et al., Obes Res 2005; 13:93-100) suggests that people associate the amount of consumed calories/meal volume and accompanying satiety feeling with what they believe they saw themselves eating, rather than with how much they actually ate. This implies that if people believe to have consumed a relatively small volume of food, they are likely to feel less satiated then in case they believe to have consumed a relatively large volume.

Consequently, the consumption of decreased portion sizes during dieting leaves consumers with cognitive/mental and physical perception that this reduced amount of food is insufficient. Thus, consumers are left with the nagging feeling that their stomach is still 'empty' and find it difficult to comply with the diet. In order to overcome this problem, nutritionists have introduced the concept of food energy density, which is defined as the number of calories per given weight of food and recommend to eat foods with a low energy density. One way to achieve this is to eat products which by nature are low in energy density (e.g. high fibre fruits and vegetables) and to avoid eating energy dense products (e.g. full-fat mayonnaise, fatty meat, cakes etc.).

Another way to decrease the energy density of foods is to dilute them with non-caloric material, e.g. water or air. A large number of literature studies have confirmed that the addition of water to lower energy density increases immediate feelings of satiety and decreases subsequent food intake. The effects of simple additions of water, however, tend to be rather short-lasting (20-60 minutes). Furthermore, the addition of water is often found to adversely affect the eating quality of the edible product.

Rolls et al., Am J Clin Nutr 2000; 72:361-8 report the results of a study that examined the effect of food volume on satiety, independent of energy density (kJ/g). The design of the study was as follows: In a within-subjects design, 28 lean men consumed breakfast, lunch, and dinner in the laboratory 1 d/wk for 4 wk. On 3 d, participants received a preload 30 min before lunch and on 1 d no preload was served. Preloads consisted of isoenergetic (2088 kJ), yogurt-based milk shakes that varied in volume (300, 450, and 600 mL) as a result of the incorporation of different amounts of air. Preloads contained identical ingredients and weighed the same. It was found that the volume of the milk shake significantly affected energy intake at lunch ($P<0.04$) such that intake was 12% lower after the 600 mL preload than after the 300 mL preload. Furthermore it is stated that subjects reported greater reductions in hunger and greater increase in fullness after consumption of both the 450 and 600 mL preloads than after the 300 mL preload. However, the authors also conclude that "Subjects overate compared with the control condition (4199±193 kJ) in the 300 mL (5456±196 kJ), 450 mL (5233±180 kJ) and 600 mL conditions (5054±246 kJ). Therefore, it can be concluded from this study that the consumption of the preloads failed to induce a level of satiety that resulted in the consumption of less energy.

Edible foam products of pourable or spoonable consistency are known in the art. EP-A 0 292 034 describes a foamable product consisting of a homogenized mixture of fat, protein, water, alcohol and a calcium source containing lactates and/or polyphosphate. It is observed that foaming of the foamable product can be performed by whisking or from an aerosol can. The resulting foam is said to be stable in a temperature range of −8 to 50° C. when using alcohol up to a maximum alcohol content of 40 vol. % and to acid up to a pH of about 2.

U.S. Pat. No. 3,809,764 describes low caloric food compositions comprising an aqueous foam containing water, polyglycerol ester as foaming agent, a hydrophilic colloid as stabilizer and optional ingredients. Example A describes the preparation of a whipped imitation butter that is said to be stable for several days at room temperature.

U.S. Pat. No. 5,000,974 describes aerated food products formed by aerating a fruit base comprising fruit or fruit extract base, locust bean flour, pectin, carrageenan and water. The aerated food products are said to be structure-stable, temperature-insensitive as well as inexpensive.

WO 2006/067064 describes a shelf stable mousse comprising a food composition based on condensed milk aerated with an inert gas, wherein the food composition contains a foam stabilizer and has a fat content of les than 25% by weight. It is stated in the international patent application that the shelf stable mousse does not need to be stored in a refrigerated environment.

SUMMARY OF THE INVENTION

The inventors have developed edible products of low energy density that following consumption produce strong as well as long-lasting satiety feelings. The solution provided by the inventors is an edible product in the form of a foam of pourable or spoonable consistency, which foam contains at least 60 wt. % of water, from 1 to 7 wt. % of protein and from 1 to 20 wt. % of carbohydrates, and is characterised by an exceptionally high in-mouth and gastric stability.

Due to the relatively high volume of the present foam product, the consumption of one voluminous portion of such a foam product is experienced by a consumer as more filling than an identical portion of the same product with a much higher density. Furthermore, the consumption of the present product produces much more pronounced satiety fillings than a similar foam product that lacks the in-mouth stability of the present foam product. In addition, due to the fact that the present foam product, unlike conventional aerated food products, is capable of retaining its foamy nature in the stomach, its consumption produces an enhanced feeling of 'fullness'. Finally, the very high gastric stability of the foam ensures that the feeling of fullness lingers, especially as the gastric stability of the foam product is believed to result in delayed gastric emptying.

Since the edible foam products of the present invention contain protein and carbohydrates, these products can advantageously be designed as meal replacers, meal components, snacks or clinical food.

Another advantage of the edible foam products of the present invention resides in the fact that their eating quality is excellent as they combine exceptional gastric and in-mouth stability with a pleasant creamy texture. Furthermore, unlike many conventional food products of low energy density, notably products that contain elevated levels of water, also the taste of the present edible foamed products is highly appreciated by consumers.

Another aspect of the invention relates to a pressurised container holding an edible liquid composition and a propellant, which liquid composition can be released from the container by activating a valve to produce an edible foam product with high gastric stability.

Yet another aspect of the invention relates to an edible foam product with high gastric stability for use in the treatment or prevention of overweight or obesity.

DETAILED DESCRIPTION OF THE INVENTION

Figure 1:
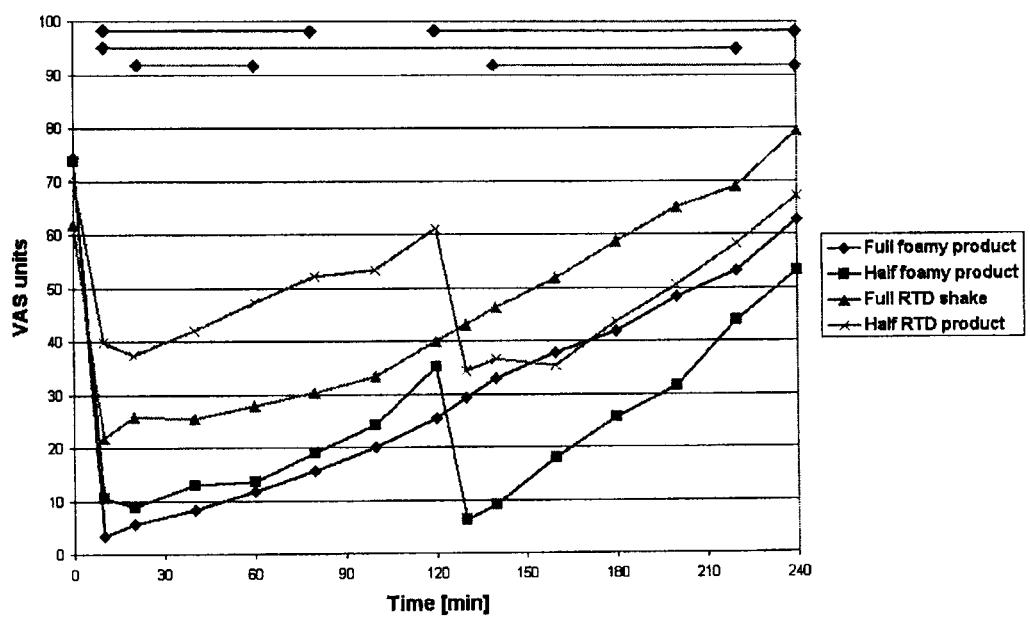
FIG. 1 is a chart of AUC (top) and a graph (bottom) of data for hunger. In the AUC chart, the top lines depict the differences between full foamy product and full RTD shake, the middle line depicts the differences between half foamy product and half RTD shake, and the bottom lines depict the differences between half foamy product and full RTD shake. Statistics are based on two-sided Fisher analysis, with baseline as covariant (p<0.05).

Accordingly, one aspect of the invention relates to an edible foam product of pourable or spoonable consistency having an overrun of at least 100%, said foam product containing at least 60 wt. % of water, from 1 to 7 wt. % of protein and from 1 to 20 wt. % of carbohydrates, and further being characterised by a very high in-mouth and gastric stability. The high gastric stability of the foam product is apparent from the time ($t_{1/2}$) needed to achieve a reduction in overrun of 50% under gastric conditions. The foamed product of the present invention exhibits a $t_{1/2}$ of more than 30 minutes. The high in-mouth stability of the present foam product is evidenced by a reduction in overrun of less than 35% when a sample of the product is subjected to a stability test in which conditions of shear are applied that are similar to those observed in the mouth.

The aforementioned parameter $t_{1/2}$ is determined in a gastric stability test involving combining 400 ml of the foam product with 15 ml of an artificial gastric juice comprising 60 mg of 1:1 (wt) pepsin/lipase mix (pepsin from hog stomach, activity 724 U/mg, Fluka BioChemika, cat. no. 77160; lipase from *Rhizopus oryzae*, activity 53 U/mg, Fluka BioChemika, cat. no. 80612) in 1M HCl containing 150 mM NaCl and 5 mM KCl. The foam product is placed in a glass cylinders (length 200 ml, diameter 60 ml) and the artificial gastric juice is poured on top of the foam product. The cylinders are placed in a thermostated shaking water bath (37° C.), operating at a shaking rate of 1.2 $s^{-1}$, while the stability of the foam product is monitored.

The satiety inducing impact of the present edible foam product is particularly pronounced in case the foam structure of the product is hardly affected by the shear that is exerted on the product during mastication. The inventors have managed to design edible foam products that, unlike conventional food foams, such as e.g. ice cream, whipped cream, mousses and bread, do not undergo a drastic decrease in foam volume and overrun when subjected to shear at ambient or physiological temperature. The in-mouth stability of a foamed product as referred to in this document is determined by introducing a predetermined volume of an edible foam product in a glass funnel (diameter 100 mm, neck length 100 mm, neck diameter 10 mm), which is connected to a silicone tube (length 400 mm, diameter 12×8 mm). The middle part of the silicone tube is inserted into a peristaltic pump Verderflex 2010 (Verder Ltd, Leeds, UK) operating at 60 rpm. After the processing in the peristaltic pump the sample is collected in a glass measuring cylinder and the product volume and product weight are measured immediately.

According to a preferred embodiment, the edible foam product of the present invention has an overrun of at least 150%, more preferably of at least 180%. The overrun of a foam product is calculated using the following equation:

$$\text{Overrun} = 100\% \times (V_{foam\,product} - V_{mix}) / V_{mix}$$

$V_{foam\,product}$ = Volume of a sample of the edible foam product
$V_{mix}$ = Volume of the same sample after the dispersed gas phase has been removed The edible foam product of the present invention typically contains at least 50 vol. % of a dispersed gas phase (which equates to an overrun of 100%). Preferably, the product contains at least 60 vol. % of a dispersed gas phase. The vol. % of gas phase (φ) contained in the present product may suitably be determined by measuring the density of pre-aerated solution, $\rho_0$, and the density of the foamed product, $\rho_f$, and applying the following equation: $\phi=100(1-\rho_f/\rho_0)$ and is related to the overrun as follows: $\phi=100$ Overrun/(100+Overrun). The gas phase in the present product can comprise air or any other gas that is considered safe for food applications.

In the shear test described above the foamed products of the present invention typically show a reduction in overrun of less than 30%, preferably of less than 25%, most preferably of less than 22%. In contrast, known edible foam products, such as chocolate mousse and whipped cream, show decreases in overrun that are well in excess of these percentages.

According to another preferred embodiment, the product obtained from the in-mouth stability test described above still exhibits an overrun of at least 100%, more preferably of at least 150%. Edible foam products that are capable of retaining a high overrun when subjected to conditions of shear that are similar to those observed during mastication and that additionally exhibit high stability under gastric conditions are extremely useful for inducing prolonged satiety feelings.

According to a particularly preferred embodiment, the aforementioned criteria are also met by the present foam product if the shear stability test is conducted at a temperature of 37° C., thus reflecting the prolonged in-mouth stability of the product under conditions of shear that are similar to those exerted during mastication.

The edible foam product according to the present invention can suitably be produced on an industrial scale. According to a preferred embodiment, the present edible foam product has been pasteurised or sterilised in order to increase it shelf-life. Most preferably, the product has been sterilised.

The benefits of the present product are particularly pronounced in case the in-mouth and gastric stability is very high. Accordingly, in a particularly preferred embodiment $t_{1/2}$ exceeds 45 minutes, even more preferably it exceeds 60 minutes, even more preferably it exceeds 90 minutes and most preferably $t_{1/2}$ exceeds. 120 minutes.

The benefits of the present invention may be obtained with any type of edible foam, as long as it exhibits sufficient in-mouth and gastric stability.

The inventors have discovered that the gastric stability of the present product may be enhanced considerably by incorporating an anionic polysaccharide that is capable of forming a gel in the presence of a multivalent cation such as $Ca^{2+}$. Suitable examples of such anionic polysaccharides include alginate and pectin. Although the inventors do not wish to be bound by theory it is believed that under the prevailing acidic conditions of the stomach, anionic polysaccharides will form a gel that helps to stabilise the foam structure. Thus, according to a preferred embodiment, the edible foam product contains from 0.1 to 5.0 wt. % of anionic polysaccharide selected from the group of alginate, pectin and combinations thereof.

In order to ensure that sufficient calcium is present to ensure that the anionic polysaccharide forms a gel, it is preferred to include multivalent, e.g. divalent and/or trivalent metal cations in the product. Examples of suitable metal cations include $Ca^{2+}$, $Fe^{2+}$, $Fe^{3+}$, $Cu^{2+}$ and/or $Mg^{2+}$. Advantageously, these metal cations are incorporated in the form of undissolved salt, especially undissolved salts that become much more soluble under acidic conditions. Thus, it is possible to provide a product that exhibits a soft or pourable texture when eaten, but that forms a firm foam structure in the stomach due to the gelation of the anionic polysaccharide.

Preferably, the edible foam product contains from 0.01-1 wt. %, more preferably from 0.02-0.8 wt. % of non-dissolved calcium salt. The non-dissolved calcium salt is advantageously selected from the group consisting of e.g. calcium carbonate, calcium phosphate and combinations thereof.

The present product typically has a pH within the range of 5.5 to 8.0. Most preferably the pH of the product is within the range of 6.0 to 7.5. As explained herein before, a non-acidic pH offers the advantage that it enables the preparation of an edible foam product that is pourable or that has a soft texture, but that will form a firm foam under gastric conditions.

Edible foam products of very high gastric stability may suitably be prepared by employing at least 0.1 wt. %, preferably at least 1 wt. % of a protein selected from the group consisting of soy protein, egg protein and combinations thereof. According to a particularly preferred embodiment, the present product contains at least 3 wt. % of soy protein.

In accordance with another advantageous embodiment of the invention, the edible foam product contains at least 0.01 wt. % of a foam stabilising protein selected from the group consisting of hydrophobin, chaplin and combinations thereof.

It was found that the in-mouth and gastric stability of the present edible product can be enhanced by the inclusion of amphipathic particles, especially if the product is water-based. It is believed that these particles have a stabilising effect on water-air interface. Advantageously, the present product contains from 0.1 to 10 wt. %, more preferably 0.5-2 wt. % of amphipathic particles. The term "amphipathic particles" as used herein refers to particles that largely consist of material that is balancedly wetted by water and air. Thus, the term amphipathic particles does not, for instance, encompass fat globules, which are very hydrophobic i.e. wetted only by oil (air) or calcium carbonate or microcrystalline cellulose which are very hydrophilic i.e. wetted only by water.

Best results are obtained in case the amphiphatic particles have a volume weighted mean diameter in the range of 0.02 to 10 μm, especially in the range of 0.2 to 2 μm. Examples of amphiphatic particles that may suitably be employed in accordance with the present invention include cocoa powder, surface active fibres, modified celluloses, modified starches, mineral particles, clays, protein particulates and combinations thereof. It was found that the wettability of the amphiphatic particles is correlated with their foam stabilising capacity. Preferably, the amphiphatic particles are characterised by the averaged contact angle of the particle-aqueous phase-air interface, which in turn is correlated with the stabilising capacity of these same particles. Preferably, said contact angle is within the range of 60 to 120°, more preferably it is within the range of 70-110°.

The edible foam product of the invention advantageously contains from 0.1 to 10 wt. % of fat. The fat contained in the product may contribute to the stability of the foam, especially if a significant fraction of the fat is solid at body temperature. Thus, in accordance with a particularly preferred embodiment, the fat contained in the edible foam product has a solid fat content at 37° C. of at least 5%, more preferably of at least 10% and most preferably of at least 15%. The solid fat content may suitably be determined by NMR-methods that are well-known the person skilled in the art.

The edible foam product of the present invention advantageously contains less than 4 wt. %, preferably less than 1 wt. % of alcohol. Most preferably, the edible foam product contains no alcohol.

In accordance with another preferred embodiment, the present foam product contains less than 0.3 wt. %, more preferably less than 0.1 wt. % of polyglycerol ester. Most preferably, the product does not contain polyglycerol ester.

The present foam product may suitably contain sugar (sucrose). Preferably, however, the sugar content of the foam product is less than 5 wt. %, more preferably less than 3 wt. % and most preferably less than 2 wt. %.

The edible foam product of the invention may be pourable or spoonable. According to one embodiment, the product is non-pourable. Such a non-pourable product typically exhibits spoonable rheology defined as follows: yield value of >50 Pa, when extrapolating from shear rates between 100 and 300 s$^{-1}$, a Bingham viscosity <500 mPa·s between shear rates of between 100 and 300 s$^{-1}$, a failure at stress at a strain of <0.5 Radians. The yield stress is determined at a temperature of 20° C. using a Haake VT550 viscometer According to another embodiment, the edible foam product is pourable. A pourable product offers the advantage that it can be drunken. If the product is drunken rather eaten, the chance of undesirable density increase as a result of mastication is minimised—for example bread is high overrun product, but practically all air is lost during mastication. In particular, in case the edible foam product is stabilised in the stomach due to the gelling action of anionic polysaccharide, it is advantageous to employ an edible foam product in pourable form.

The edible foam product of the present invention may be a sweet or a savoury product. Sweet products may suitably be consumed as a snack or a meal component. An example of a pourable sweet foam product is a milkshake-like product, fruit smoothes etc. Spoonable sweet foam products may resemble products such as chocolate or vanilla mousse, flan, ice cream, whip cream etc. Savoury products may be consumed as a snack, a meal component or even a meal replacer. An example of a savoury foam product is a savoury mousse, e.g. poultry, fish, or shellfish mousses or foie gras.

It is noted that the present invention also encompasses composite food products that contain the present edible foam product. Thus, the present invention encompasses, for instance, a filled bar in which the edible foam product constitutes the filling. The invention also encompasses a multilayered food product containing the present edible foam product and layers made of different edible materials, e.g. meat, noodles, vegetables, bread, fruit, chocolate, cake, wafer or ice cream.

In order to enhance the effectiveness of the present product in the treatment or prevention of obesity it is preferred that the caloric content of the product is limited. Typically, the present product has a caloric density of not more than 0.5 kcal/ml. Although it is feasible to provide an edible foam product according to the present invention with very low caloric content, the caloric density preferably exceeds 0.05 kcal/ml. Most preferably, the caloric density of the edible foam product is in the range of 0.1-0.3 kcal/ml.

According to another preferred embodiment, the present edible foam product contains:
1-10 wt. % of protein;
0.5-5 wt. % of fat;
1-10 wt. % of carbohydrate; and
at least 80 wt. % of water.

In terms of caloric contribution the preferred amounts of protein, fat and carbohydrate are as follows:
10-40 cal. % of protein;
5-30 cal. % of fat; and
10-60 cal. % carbohydrates.

Carbohydrates that may suitably be employed in the present product include, besides the aforementioned anionic polysaccharides, monosaccharides (e.g. glucose, fructose and invert sugar), disaccharides (e.g. sucrose or lactose), oligosaccharides (e.g. fructooligosaccharids, maltodextrin) and polysaccharides (e.g. inuline, starch). Preferably, the combined amount of mono- and disaccharides in the present edible foam product is within the range of 0.25-10 wt. %.

The edible foam product of the present invention is advantageously consumed as a meal replacer or a meal component. Besides proteins, carbohydrates and/or fat, the present product advantageously contains essential (micro)nutrients such as vitamins, minerals, flavonoids, sterols and anti-oxidants. Other ingredients that may suitably be contained in the present edible foam product include flavourings, colourings, emulsifiers etc. Naturally, the present edible foam product may also contain a variety of plant materials such as fruit juices, fruit extracts, vegetable extracts, herbs, spices etc.

The gas bubbles contained within the edible foam product can vary widely in size. Typically, the air bubbles in the product have a volume weighted mean diameter in the range of 5-500 μm, preferably of 10-200 μm. The volume weighted mean diameter of the gas bubbles is suitably determined by means of optical microscopy.

The inventors have found that the stability of the edible foam product, especially if it is produced in situ from a pressurised aerosol system, is affected by the composition of the gas that is retained within the foam. In order to generate a very stable foam, it is advantageous to include a gas that has limited water-solubility. Air, for instance, is not particularly suitable as e.g. oxygen has a relatively high solubility in water.

According to a particularly preferred embodiment, the edible foam product of the present invention contains a gas that is less soluble in water than air (at a temperature of 37° C. According to another preferred embodiment, relative to air, the gas contained in foam product contains elevated levels of one or more of the following gasses: $N_2$, $N_2O$, $CO_2$, He, $O_2$. Here the term "elevated" means that the concentration of at least one of said gasses is at least 10% higher than in air.

Another aspect of the present invention relates to the use of an edible foam product in the treatment or prevention of overweight or obesity, said edible foam product being characterised by a pourable or spoonable consistency, an overrun of at least 100% and a very high gastric stability as evidenced by $t_{1/2}$>30 minutes. The aforementioned treatment preferably comprises ingestion, i.e. oral administration of a foodstuff or nutritional product comprising the edible foam product. In order to achieve the desired satiety effect, it is preferred that at least 100 ml of the edible foam product is consumed per administration event. Thus, the preferred serving size is at least 100 ml. Most preferably, the serving size is within the range of 300-800 ml. According to a particularly preferred embodiment, the edible foam product employed in the treatment or prevention of overweight or obesity is an edible foam product exhibiting both gastric and in-mouth stability as defined herein before.

Yet another aspect of the invention relates to a pressurised container holding an edible liquid composition and a propellant, which liquid composition can be released from the container by activating a valve to produce an edible foam product, said edible foam product being characterised by a pourable or spoonable consistency, an overrun of at least 100% and a very high gastric stability as evidenced by $t_{1/2}$>30 minutes. Typically, the density of the edible foam product thus obtained has a density that is much lower (e.g. 40% lower) than that of the liquid composition in the container. According to a preferred embodiment, the edible foam product produced upon activation of the valve has the same composition as the edible liquid composition (gas phase not being included).

Suitable propellants include compressed gasses, especially liquefied gasses. Preferably, the propellant employed is selected from $N_2O$, $N_2$, $CO_2$, air and combinations thereof.

Most preferably, the propellant employed is selected from $N_2O$, $N_2$, $CO_2$ and combinations thereof.

Typically, the propellant contained in the pressurised container has a pressure of at least 3 bar. Usually, the said pressure does not exceed 12 bar.

The invention is further illustrated by means of the following examples.

EXAMPLES

Example 1

Liquid formulations were prepared using the following recipes (concentrations in wt. %):

| Ingredient | Product 1A | Product 1B |
|---|---|---|
| Skimmed milk powder | 6.10 | 6.40 |
| Calcium caseinate | 1.60 | 1.60 |
| Milk protein concentrate | 1.30 | 1.10 |
| Maltodextrin (DE = 5) | 1.30 | 1.30 |
| Cocoa powder | 1.20 | |
| Sucrose | 1.00 | 1.00 |
| Sunflower oil | 0.90 | 0.90 |
| Microcrystalline cellulose | 0.60 | 0.60 |
| Gum Arabic | 0.60 | 0.60 |
| Monoglyceride | 0.50 | 0.50 |
| Dipotassium phosphate | 0.16 | 0.16 |
| Lecithin | 0.10 | 0.10 |
| Carrageenan | 0.09 | 0.07 |
| Water | 84.55 | 85.67 |

The liquid formulations were prepared as follows:

All dry ingredients except lipids were dispersed in warm water (60° C.) using agitation with a high-shear mixer (Silverson™, Emulsor™ screen, 6000 rpm) for 5 min. Then preheated lipid mixture (60° C.) was added to the aqueous base solution upon continuous mixing with a Silverson™. Pre-emulsion was then homogenized at 65° C. and 225 bar in a high-pressure homogenizer (Niro Soavi™), sterilized for 10 sec at 142° C., cooled down to 65° C. and post-homogenized at 50 bar. Finally, emulsions were rapidly cooled to ambient and aseptically bottled in sterile Nalgene™ bottles.

Next, 330 ml of each liquid formulation was poured into a pressurisable dispenser (cream whipper "Gourmet Whip", 0.5 l, art. nr. 243110, iSi GmbH, Vienna, Austria). The dispenser was closed and a screw type N2) gas charger was mounted on the dispenser until gas was released therefrom. The dispensers was shaken for about 10 seconds, following which the contents were released. The in-mouth and gastric stability of the edible foam products so obtained was determined using the methodology described herein before. For comparison the in-mouth stability of a commercially available whipped cream (Slagroom, Melkan, Postbus 80, 4153ZH, Beesd, The Netherlands) was also measured. In this case the cream was aerated by using its original aerosol dispenser can. The results so obtained are depicted below.

| | Product 1A | Product 1B | Whipped cream |
|---|---|---|---|
| Initial overrun (OV) | 238% | 213% | 325% |
| In-mouth stability loss (% of lost OV) | 18% | 31% | 68% |
| Gastric stability | $t_{1/2}$ = 140 min. | $T_{1/2}$ = 55 min. | $T_{1/2}$ = 55 min. |

Example 2

A consumer study was conducted to determine the effect on satiety of an edible foam product according to the present invention. In this study the foam product 1B described in Example 1 was compared with a liquid, i.e. non-foamed product of identical composition. The foam product used in the study was actually prepared from the same liquid formulation that was used as a comparison.

The design of the consumer study was as follows:
Subjects:

Twenty-four healthy volunteers, aged between 18 and 60 years and with a body mass index between 21.0 and 32.0 $kg/m^2$, were selected for this study. Volunteers were selected upon the following criteria: they had to be Slim•Fast® users, they had to like chocolate flavour and they had to be available on specific test days. Two thirds of the volunteers had been previously involved in a similar satiety study.

Experimental Design:

The study had a randomised and cross-over design. The experimental design consisted of four test days with four treatments:

① Liquid product (325 ml, 190 kcal) ingested at a single time=0 min
② Foam product (ca. 1000 ml, 190 kcal) ingested at a single time=0 min
③ Half liquid product (162.5 ml, 95 kcal) ingested twice, i.e. at time=0 min and time=120 min
④ Half foam product (ca. 500 ml, 95 kcal) ingested twice, i.e. at time=0 min and time=120 min The volunteers were asked to consume their breakfast before 10.00 a.m. They arrived at the Consumer Test Centre between 11.50 and 12.00 h. There they were seated in the same room (twelve volunteers on each test day) with the possibility to talk to each other.

The volunteers completed a questionnaire on appetite, mood and stomach complaints (baseline measures) immediately before seeing and consuming the treatment. At 12.00 a.m. they consumed the test product. They were instructed to drink the test product within 10 min. However, some volunteers complained that the foamy product was too thick and not drinkable, so they were allowed to use a spoon.

At 12.10 a.m. the volunteers completed another questionnaire on appetite, mood and stomach complaints and a questionnaire on taste and liking. Thereafter, they left the Consumer Test Centre and continued to complete the questionnaires on appetite, mood and stomach complaints every 20 min for a total of 240 min until 4.00 a.m.

The volunteers that received the half RTD shake or the half foamy product returned to the Consumer Test Centre between 1.50 and 2.00 a.m. They again completed a questionnaire on appetite, mood and stomach complaints immediately before seeing and consuming the second half of the treatment. At 2.00 a.m. they consumed the second half of the test product, after which they completed another questionnaire on appetite, mood and stomach complaints and a questionnaire on taste and liking. Thereafter, they left the Consumer Test Centre and continued to complete the questionnaires on appetite, mood and stomach complaints every 20 min until 4.00 a.m.

At 4.00 a.m., the volunteers were also asked to answer a number of open questions relative to product liking/disliking, the test method and the consumption experience.

The volunteers were asked to be consistent with respect to food and drink intake and exercise/physical activity during the test days. They were not allowed to eat and drink between 12.00 and 4.00 a.m. other than the test products and with exception of water, coffee and tea (without cream and sugar, but sweeteners were allowed), and other non-caloric beverages.

Measurements:

Questionnaires on appetite (hunger, fullness, desire to eat a snack, desire to eat a meal, thirst), mood (energetic, weak/drained) and stomach complaints were rated on 100-mm Visual Analogue Scales (VAS) using a paper form, anchored at the low end with the most negative or lowest intensity feelings (e.g., not at all), and with opposing terms at the high end (e.g., extremely). Volunteers were asked to indicate on a line which place on the scale best reflects their feeling at that moment. In the analyses the scores on the VAS were assigned values from 0 to 100 VAS units (=mm).

Additionally, questionnaires on taste and liking of the test product (overall liking, taste/flavor liking, smell/aroma liking, mouthfeel liking) were rated on 100-mm paper Visual Analogue Scales (VAS) immediately after consumption of the test products.

Figure 2:
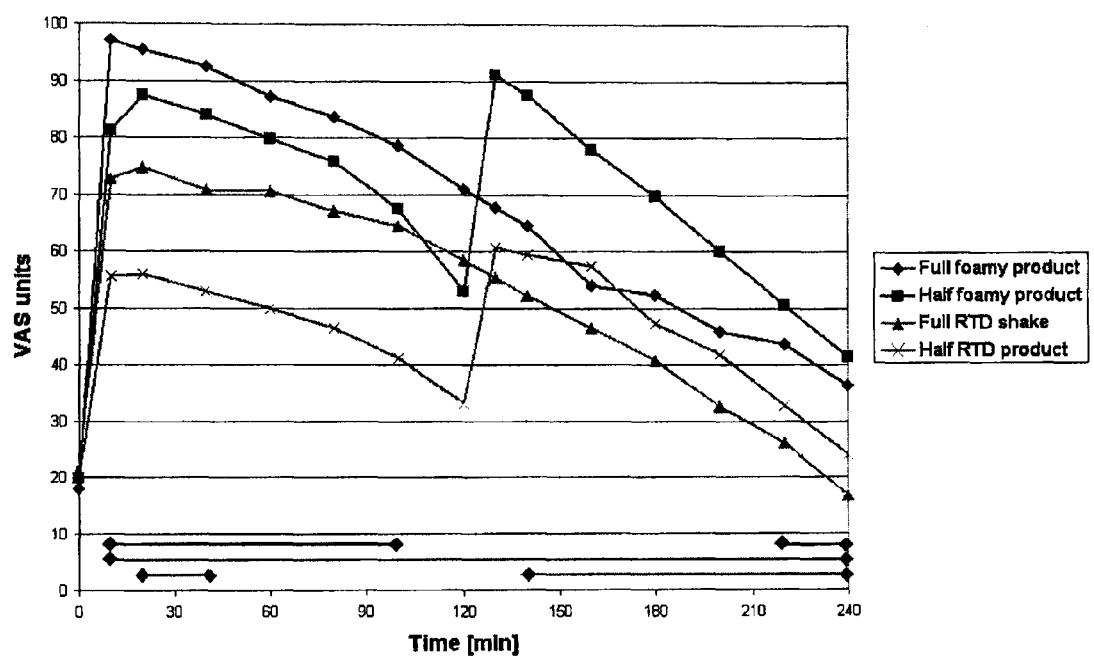
FIG. 2 is a chart of AUC (bottom) and a graph (top) of data for fullness. In the AUC chart, the top lines depict the differences between full foamy product and full RTD shake, the middle line depicts the differences between half foamy product and half RTD shake, and the bottom lines depict the differences between half foamy product and full RTD shake. Statistics are based on two-sided Fisher analysis, with baseline as covariant (p<0.05).
Figure 3:
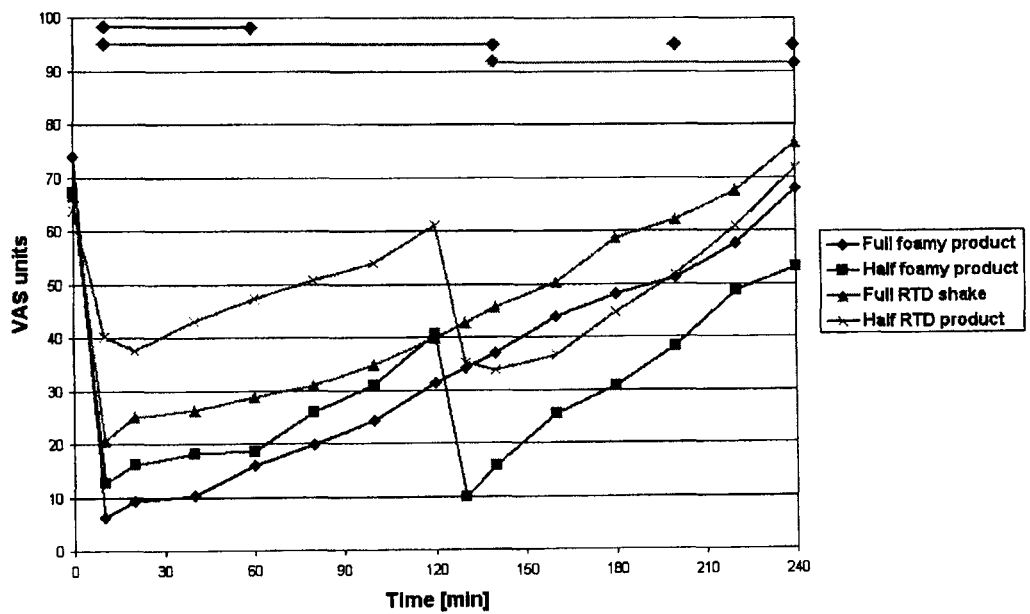
FIG. 3 is a chart of AUC (top) and a graph (bottom) of data for desire to eat a snack. In the AUC chart, the top line depicts the differences between full foamy product and full RTD shake, the middle line depicts the differences between half foamy product and half RTD shake, and the bottom line depicts the differences between half foamy product and full RTD shake. Statistics are based on two-sided Fisher analysis, with baseline as covariant (p<0.05).
Figure 4:
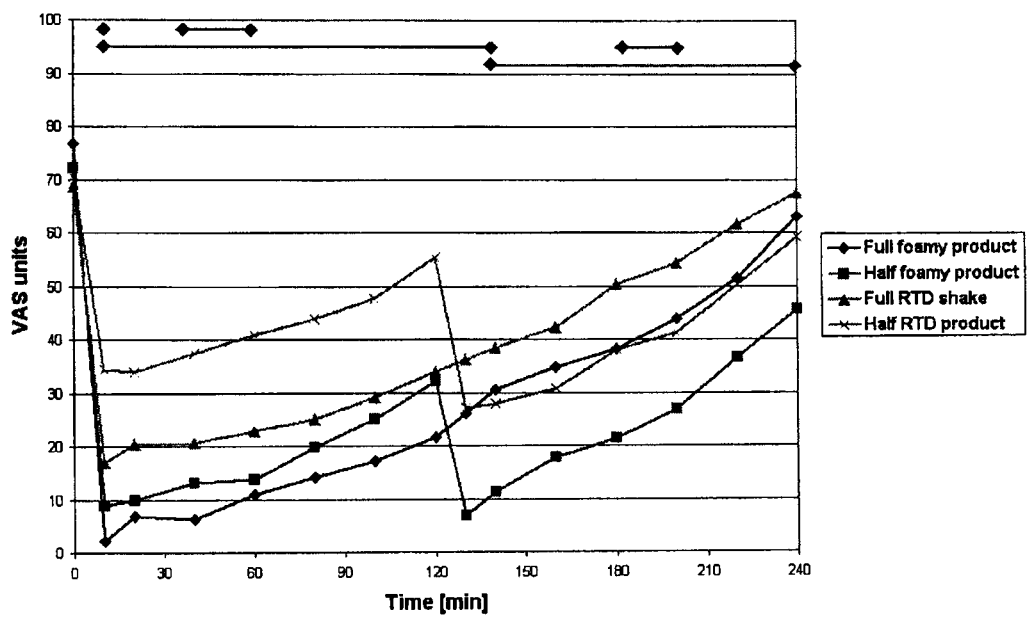
FIG. 4 is a chart of AUC (top) and a graph (bottom) of data for desire to eat a meal. In the AUC chart, the top line depicts the differences between full foamy product and full RTD shake, the middle lines depict the differences between half foamy product and half RTD shake, and the bottom line depicts the differences between half foamy product and full RTD shake. Statistics are based on two-sided Fisher analysis, with baseline as covariant (p<0.05).

At the end of the test, the volunteers were asked to answer a number of open questions relative to how they liked/disliked the test product, the test method and the consumption experience. They also had to rate how likely they would purchase the test product on a 5-point scale. These questions are shown in FIG. 2c.

Statistical Analysis:

Statistical analysis was assessed by using analysis of variance (ANOVA) with subjects, periods and treatments as factors. Baseline values were taken into account as a covariable. Differences between treatments (full foamy product vs. full RTD shake, half foamy product vs. half RTD product, half foamy product vs. half RTD product) were established using the Bonferroni post-hoc test. A p-value <0.05 (two-sided) was considered significant.

Results:

Twenty-four healthy volunteers (3 men, 21 women), aged (mean±SD) 41.8±8.8 y (range 28-60 y) and with a body mass index of (mean±SD) 26.2±2.4 kg/m² (range 22.1-31.2 kg/m²) were recruited and completed the study.

The foam product consumed as a single portion, was found to significantly reduce hunger, desire to eat a snack, desire to eat a meal, and enhanced fullness compared to the liquid product that was consumed as a single portion. Although a significant effect for reduced hunger and enhanced fullness was observed throughout the entire 240 min, the effect on desire to eat a snack or desire to eat a meal mainly occurred during the first 120 min.

The foam product ingested in two portions was found to significantly reduce hunger, desire to eat a snack, desire to eat a meal, and enhanced fullness compared to the liquid product that was consumed in two portions. The effect on these parameters was observed throughout the entire 240 min, but was stronger between 120 and 240 min Curves and AUC data for hunger, fullness, desire to eat a snack and desire to eat a meal are shown in FIGS. 1-4.

Example 3

Liquid formulations were prepared using the following recipes and using the methodology described in Example 1 (concentrations in wt. %):

| Ingredient | Product 3A | Product 3B |
|---|---|---|
| Skimmed milk powder | 6.50 | 6.50 |
| Sucrose | 6.50 | 6.50 |
| Sunflower oil | 0.40 | 0.40 |
| Gum Arabic | 1.10 | 1.10 |
| Calcium caseinate | 0.80 | 0.80 |
| Microcrystalline cellulose | 0.60 | 0.60 |
| Dipotassium phosphate | 0.16 | 0.16 |
| Lecithin | 0.10 | 0.10 |
| Monoglyceride | 0.07 | 0.07 |
| Carrageenan | 0.02 | 0.02 |
| Alginate | | 0.6 |
| Pectin | | 0.4 |
| Water | 83.75 | 82.75 |

Foam products were produced from the liquid product using a pressurised dispenser as described in Example 1 and the gastric stability of the foam products was determined. The following results were obtained:

| | Product 3A | Product 3B |
|---|---|---|
| Gastric stability | $t_{1/2} = 6$ min. | $t_{1/2} > 150$ min. |

Example 4

Liquid formulations were prepared using the following recipes and using the methodology described in Example 1 (concentrations in wt. %):

| Ingredient | Product 4A | Product 4B |
|---|---|---|
| Skimmed milk powder | 5.90 | 5.90 |
| Sucrose | 2.10 | 2.10 |
| Cocoa powder | 1.20 | 1.20 |
| Soy protein isolate | 0.90 | 0.90 |
| Gum Arabic | 0.65 | 0.65 |
| Microcrystalline cellulose | 0.60 | 0.60 |
| Monoglyceride | 0.04 | 0.04 |
| Dipotassium phosphate | 0.25 | 0.25 |
| Lecithin | 0.10 | 0.10 |
| Carrageenan | 0.06 | 0.06 |
| Pectin | | 0.4 |
| Alginate | | 0.6 |
| Water | 88.20 | 87.20 |

Foam products were produced from the liquid product using a pressurized dispenser as described in Example 1 and the gastric stability of the foam products was determined. The following results were obtained:

| | Product 4A | Product 4B |
|---|---|---|
| Gastric stability | $t_{1/2} = 4$ min. | $t_{1/2} = 60$ min. |

Example 5

Liquid formulations were prepared using the following recipes and using the methodology described in Example 1 (concentrations in wt. %):

| Ingredient | Product 5A | Product 5B |
|---|---|---|
| Skimmed milk powder | 6.50 | 6.50 |
| Sucrose | 6.50 | 6.50 |
| Sunflower oil | 0.40 | 0.40 |
| Gum Arabic | 1.10 | 1.10 |
| Calcium caseinate | 0.80 | 0.80 |
| Microcrystalline cellulose | 0.60 | 0.60 |
| Dipotassium phosphate | 0.16 | 0.16 |
| Lecithin | 0.10 | 0.10 |
| Monoglyceride | 0.07 | 0.07 |
| Carrageenan | 0.02 | 0.02 |
| Cocoa powder |  | 1.50 |
| Water | 83.75 | 82.25 |

Foam products were produced from the liquid product using a pressurised dispenser as described in Example 1 and the gastric stability of the foam products was determined. The following results were obtained:

|  | Product 5A | Product 5B |
|---|---|---|
| Gastric stability | $t_{1/2}$ = 6 min. | $t_{1/2}$ = 40 min. |

Example 6

Liquid formulations were prepared using the following recipes and using the methodology described in Example 1 (concentrations in wt. %):

| Ingredient | Product 6A | Product 6B | Product 6C |
|---|---|---|---|
| Skimmed milk powder | 5.90 | 5.90 | 5.90 |
| Sucrose | 2.10 | 2.10 | 2.10 |
| Cocoa powder | 1.20 | 1.20 | 1.20 |
| Soy protein isolate | 0.90 | 0.90 | 0.90 |
| Gum Arabic | 0.65 | 0.65 | 0.65 |
| Monoglyceride | 0.04 | 0.04 | 0.04 |
| Dipotassium phosphate | 0.25 | 0.25 | 0.25 |
| Lecithin | 0.10 | 0.10 | 0.10 |
| Carrageenan | 0.06 | 0.06 | 0.06 |
| Cocoa powder |  | 1.50 |  |
| Microcrystalline cellulose | 0.60 | 0.60 | 2.10 |
| Water | 88.20 | 86.70 | 86.70 |

Foam products were produced from the liquid product using a pressurised dispenser as described in Example 1 and the gastric stability of the foam products was determined. The following results were obtained:

|  | Product 6A | Product 6B | Product 6C |
|---|---|---|---|
| Gastric stability | $t_{1/2}$ = 4 min. | $t_{1/2}$ = 40 min. | $t_{1/2}$ = 55 min. |

Example 7

Liquid formulations were prepared using the following recipes and using the methodology described in Example 1 (concentrations in wt. %):

| Ingredient | Product 7A | Product 7B |
|---|---|---|
| Skimmed milk powder | 5.90 | 5.90 |
| Sucrose | 2.10 | 2.10 |
| Cocoa powder | 1.20 | 1.20 |
| Soy protein isolate | 0.90 | 0.90 |
| Gum Arabic | 0.65 | 0.65 |
| Microcrystalline cellulose | 0.60 | 0.60 |
| Monoglyceride | 0.04 | 0.04 |
| Dipotassium phosphate | 0.25 | 0.25 |
| Lecithin | 0.10 | 0.10 |
| Carrageenan | 0.06 | 0.06 |
| Sunflower oil | 3.00 |  |
| Palm oil |  | 3.00 |
| Water | 85.20 | 85.20 |

Foam products were produced from the liquid product using a pressurised dispenser as described in Example 1 and the gastric stability of the foam products was determined. The following results were obtained:

|  | Product 7A | Product 7B |
|---|---|---|
| Gastric stability | $t_{1/2}$ = 5 min. | $t_{1/2}$ = 45 min. |

The invention claimed is:

1. An edible foam product of pourable or spoonable consistency having an overrun of at least 100%, the foam product comprising:
at least 60% wt. % of water, from 1 to 7 wt. % of protein, from 1 to 20 wt. % of carbohydrates, from 0.1 to 3.0 wt. % of fat, and from 0.5 to 2 wt. % of cocoa particles with a volume weighted mean diameter between 0.2 and 2 μm; and
wherein the foam product exhibits high in-mouth stability shown by a reduction in overrun of less than 25% under in-mouth shear conditions, and high gastric stability shown by a $t_{1/2}$ exceeding 60 minutes, $t_{1/2}$ representing the time needed to achieve a reduction in overrun of 50% under gastric conditions.

2. The edible foam product according to claim 1, wherein the product shows a reduction in overrun of less than 22% under in-mouth shear conditions.

3. The edible foam product according to claim 1, wherein the product shows a $t_{1/2}$ exceeding 90 minutes.

4. The edible foam product according to claim 1, further including from 0.1-5 wt. % of anionic polysaccharide selected from the group consisting of alginate, pectin and combinations thereof.

5. The edible foam product according to claim 4, further including from 0.1-1 wt. % of non-dissolved calcium salt.

6. The edible foam product according to claim 1, wherein the product has a pH within the range of 6.0 to 7.5.

7. The edible foam product according to claim 1, wherein the product contains at least one protein selected from the group consisting of soy protein, egg protein and combinations thereof.

8. The edible foam product according to claim 1, wherein the contact angle of the particle-aqueous phase-air interface of the cocoa particles is within the range of 60°-120°.

9. The edible foam product according to claim 1, wherein the fat has a solid fat content at 37° C. of at least 5%.

10. The edible foam product according to claim 1, wherein the product has a caloric density of 0.05-0.5 kcal/ml.

11. The edible foam product according to claim 1, wherein gas bubbles in the product have a volume weighted mean diameter in the range of 5-500 μm.

12. A method of treatment or prevention of overweight or obesity, comprising oral administration of an edible foam product containing at least 60% wt. % of water, 1-7 wt. % of protein, from 1 to 20 wt. % of carbohydrates, from 0.1 to 3.0 wt. % of fat, and from 0.5 to 2 wt. % of cocoa particles with a volume weighted mean diameter between 0.2 and 2 μm and being characterised by a pourable or spoonable consistency, an overrun of at least 100%, a high in-mouth stability shown by a reduction in overrun of less than 25% under in-mouth shear conditions, and a high gastric stability as evidenced by $t_{1/2}$ exceeding 60 minutes $t_{1/2}$ representing the time needed to achieve a reduction in overrun of 50% under gastric conditions.

13. The method according to claim 12, wherein the method comprises oral administration of a serving of 300-800 ml.

14. An edible foam product of pourable or spoonable consistency having an overrun of at least 100%, the foam product comprising:
   at least 60% wt. % of water, from 1 to 7 wt. % of protein, from 1 to 20 wt. % of carbohydrates, from 0.1 to 3.0 wt. % of fat, and from 0.5 to 2 wt. % of cocoa particles with a volume weighted mean diameter between 0.02 and 10 μm; and
   wherein the foam product exhibits high in-mouth stability shown by a reduction in overrun of less than 22% under in-mouth shear conditions, and high gastric stability shown by a $t_{1/2}$ exceeding 120 minutes, $t_{1/2}$ representing the time needed to achieve a reduction in overrun of 50% under gastric conditions.

* * * * *